United States Patent
Husher (10) Patent No.: US 6,572,255 B2
(45) Date of Patent: Jun. 3, 2003

(54) APPARATUS FOR CONTROLLABLY MIXING AND DELIVERING DILUTED SOLUTION

(75) Inventor: Frederick K. Husher, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 46 days.

(21) Appl. No.: 09/841,267

(22) Filed: Apr. 24, 2001

(65) Prior Publication Data

US 2002/0154567 A1 Oct. 24, 2002

(51) Int. Cl.[7] ................................. B01F 15/02
(52) U.S. Cl. ................. 366/132; 366/134; 366/136; 366/142; 366/152.4; 366/159.1
(58) Field of Search ................. 366/132, 134, 366/136, 137, 138, 142, 152.1, 152.4, 159.1, 160.1; 137/3, 5, 93, 563

(56) References Cited

U.S. PATENT DOCUMENTS

| | | | |
|---|---|---|---|
| 3,830,473 A | * | 8/1974 | Lieferman et al. |
| 3,987,808 A | | 10/1976 | Carbonell et al. |
| 4,031,912 A | | 6/1977 | Lu et al. |
| 4,045,004 A | * | 8/1977 | Berger |
| 4,259,022 A | * | 3/1981 | Folland |
| 4,299,501 A | * | 11/1981 | Patil et al. |
| 4,403,866 A | * | 9/1983 | Falcoff et al. |
| 4,474,476 A | | 10/1984 | Thomsen |
| 4,664,891 A | * | 5/1987 | Cosentino et al. |
| 4,773,764 A | * | 9/1988 | Colombani et al. |
| 4,863,277 A | * | 9/1989 | Neal et al. |
| 4,877,522 A | | 10/1989 | Toei et al. |
| 5,211,475 A | | 5/1993 | McDermott |
| 5,340,210 A | | 8/1994 | Patel et al. |
| 5,522,660 A | | 6/1996 | O'Dougherty et al. |
| 5,590,960 A | * | 1/1997 | Clinton et al. |
| 5,800,056 A | | 9/1998 | Suzuki et al. |
| 5,887,974 A | * | 3/1999 | Pozniak et al. |
| 5,924,794 A | * | 7/1999 | O'Dougherty et al. |
| 6,039,470 A | | 3/2000 | Conwell |
| 6,132,078 A | | 10/2000 | Lin |
| 6,211,956 B1 | | 4/2001 | Nicoli |
| 6,290,384 B1 | | 9/2001 | Pozniak et al. |
| 2002/0034122 A1 | * | 3/2002 | Lemke |

* cited by examiner

Primary Examiner—Charles E. Cooley
(74) Attorney, Agent, or Firm—Charles E. Wands; Mitchell E. Alter (57) ABSTRACT

A physically compact (saline) solution preparation apparatus includes a solution mixing tank coupled to sources of concentrate and diluent. A concentrate transport path is configured to both homogenize and deliver concentrate to the mixing tank, while the diluent transport path is controllably purged of potential contaminates prior to supplying the diluent to the mixing tank. A mixed solution transport path recirculates and thereby homogenizes the contents of the mixing container, and actively pumps out solution that has been mixed to a prescribed conductivity-based concentration, to one or more solution on demand storage reservoirs for respective instruments. The operation of the apparatus is based upon measured conductivity of the contents of the solution mixing tank, so that there is no need to conduct precursor volumetric measurements of either diluent or concentrate.

21 Claims, 8 Drawing Sheets

APPARATUS FOR CONTROLLABLY MIXING AND DELIVERING DILUTED SOLUTION

FIELD OF THE INVENTION

The present invention relates in general to solution mixing systems, and is particularly directed to a new and improved solution preparation apparatus, that is operative to controllably mix, store and supply a fluid containing a component diluted to a prescribed concentration, such as a diluted saline solution used for the transport of blood cells in a hematology analyzer.

BACKGROUND OF THE INVENTION

Systems employed for particulate sample analysis, such as, but not limited to, those employed in medical applications to analyze particles such as blood cells, customarily include, or are coupled with, some form of sample delivery and mixing apparatus, that prepares a respective sample, namely, places it in the physical condition necessary for acceptance and processing through a measurement flow channel of a measurement instrument. Achieving the appropriate physical condition typically involves suspending and separating the particles in a fluid that is injected into a fluid transport channel for delivery to the particle measurement (e.g., optical illumination-based) subsystem.

For example, in the case of a hematology analyzer, a prepared blood sample carrier fluid typically comprises an isotonic solution having a prescribed dilution ratio of concentrate (e.g., sodium chloride) to diluent (e.g., deionized (DI) water). A blood sample which is to be analyzed is dispensed and delivered to an input sample reservoir (for example by way of a sample-retaining test tube, or the like). The blood sample is combined with the blood sample carrier fluid. A surfactant may also be mixed into the solution in order to readily disperse the particles.

With the development of automated (computer workstation-controlled) cell analyzers, there is currently a high demand for complete, yet reasonably priced instruments that not only occupy a relatively limited amount of user space, but also are capable of high throughput and reduced operating time. One of the requirements of such systems is that they provide a continuous supply of a blood sample carrier fluid using a minimum amount of labor or floor space. In addition, there is a need to have the blood sample carrier fluid with mixture uniformity. Moreover, the blood sample carrier fluid must be compatible with test procedures for analyzing the blood sample. Still further, the system should provide safety measures for the blood sample carrier fluid storage, delivery and disposal.

SUMMARY OF THE INVENTION

In accordance with the present invention, a new and improved solution preparation and delivery architecture is provided which is operative to controllably mix, store and deliver to one or more utility devices, such as blood sample analyzing instruments, a solution of a diluent, such as deionized water, containing a prescribed concentration of a dispersed or dissolved component, such as sodium chloride. For this purpose, the solution preparation and supply apparatus includes a diluted solution mixing container, that is coupled to receive, mix and store each of a liquid concentrate of a prescribed component and a diluent. The liquid concentrate is stored in and extracted from a concentrate storage container, under the control of a supervisory processor, for delivery over a concentrate transport path to the solution mixing container.

The concentrate transport path includes a set of valve and pump components, that enable it to controllably recirculate the liquid concentrate contents of the component storage container, in order to maintain the concentrate in a homogenous state prior to its being supplied to the solution mixing container. The diluent is supplied to the mixing tank by way of a diluent transport path, coupled to a source of diluent, such as deionized water, and is configured to controllably dispense the diluent into the mixing container. To avoid the potential problem of having an unused diluent distribution line serve as a host for the growth of biological contaminants, the diluent transport path is controllably purged of potential contaminates prior to supplying the diluent to the mixing container.

A mixed solution transport path is coupled to the solution mixing container and to a prepared solution output port. The mixed solution transport path actively recirculates and thereby homogenizes the contents of the mixing container, during an iterative sequence of adding diluent to the mixing tank and conducting conductivity measurements, until the conductivity of the solution in the mixing tank reaches a target value required by a downstream instrument. The mixed solution transport path is also configured to controllably actively pump out solution that has been mixed and stored in the mixing container. The output port is coupled over a mixed solution supply line to one or more solution on demand storage reservoirs for respective instruments.

A demand valve-responsive reservoir for a respective instrument is coupled to the prepared solution supply line and may be configured as an industry standard CUBITAINER® plastic container (Hedwin Corp., Baltimore, Md.). A demand controller manages delivery of the mixed solution from the mixing container to the reservoir when its associated instrument (e.g., hematology analyzer) requires additional (saline) solution. Because the reservoir is expected to remain connected to an instrument for a long period of time, it is placed in a protective tray. The tray contains leak detectors, that monitor whether the outside of the reservoir is damp, contains a minor leak, or whether a massive leak has formed. A leak condition is determined by measuring whether the impedance between sensor pairs is less than a prescribed value.

An auxiliary (waste) tank may be coupled to the fluid transport paths for the solution mixing tank storing purged waste liquid, to accommodate the case where the facility in which the mixing tank is installed has no readily accessible floor drain for the purpose.

The preparation, mixing and delivery sequence executed by the invention employs a plurality of conductivity thresholds to reach a target solution conductivity associated with desired (saline) concentration. This enables the invention to comply with a solution specification, such as a constant conductivity isotonic solution for a hematology analyzer, that uses changes in conductivity of a fluid in a flow measurement aperture to count and recognize blood cells.

DETAILED DESCRIPTION

For purposes of providing a non-limiting example, the present invention will be described for the case of preparing a saline solution of sodium chloride dissolved in deionized water to a prescribed concentration (as determined by solution conductivity), such as may be employed to transport a blood sample through a blood cell analysis subsystem within a hematology analyzer. It should be observed, however, that the application of the invention to the preparation and delivery of saline, and its use with a hematology instrument, are given only for purposes of example and are not to be considered limitative of the structure or operation of the invention.

Figure 1:
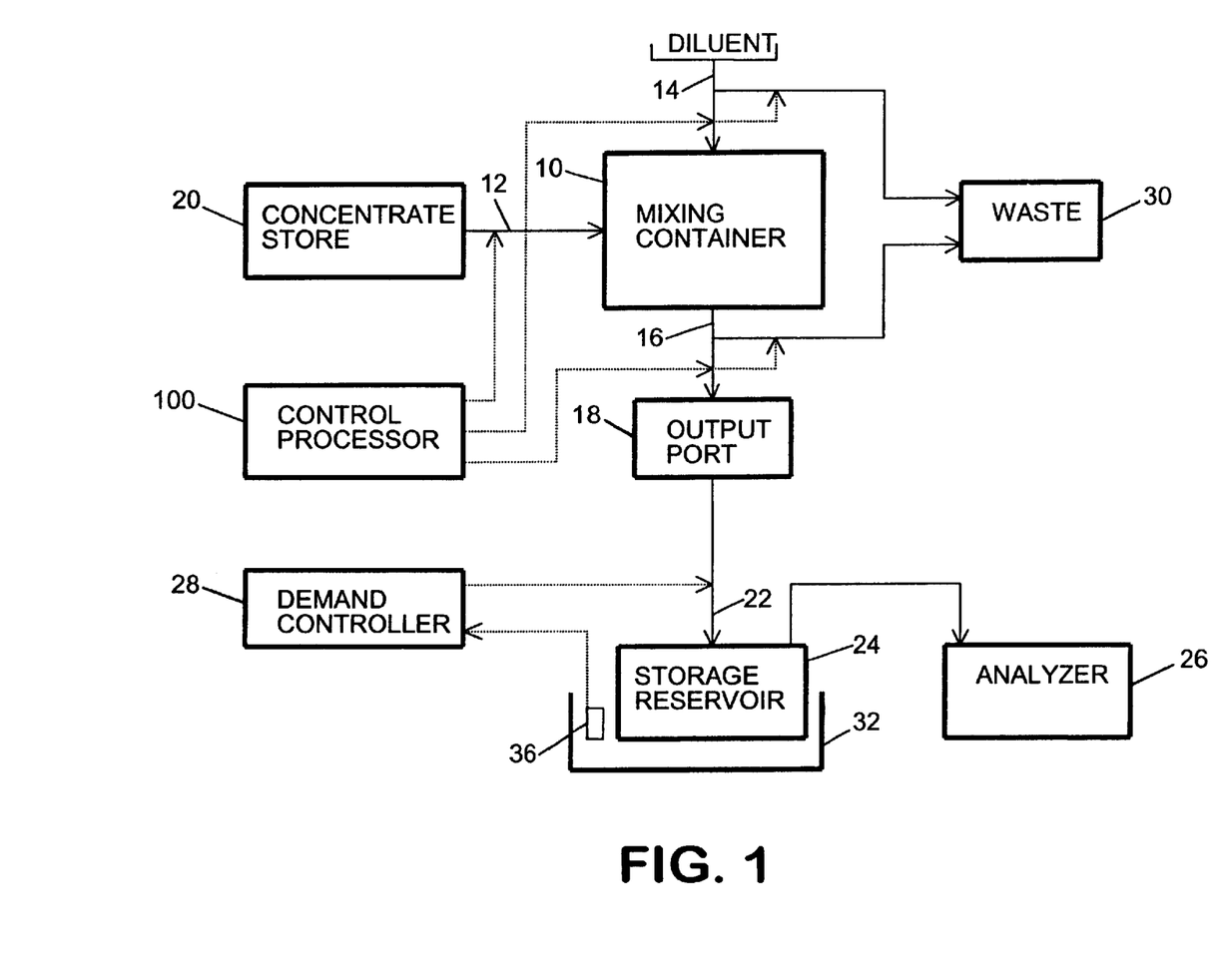
FIG. 1 diagrammatically illustrates the overall architecture of the solution preparation and delivery apparatus of the present invention.
Figure 2:
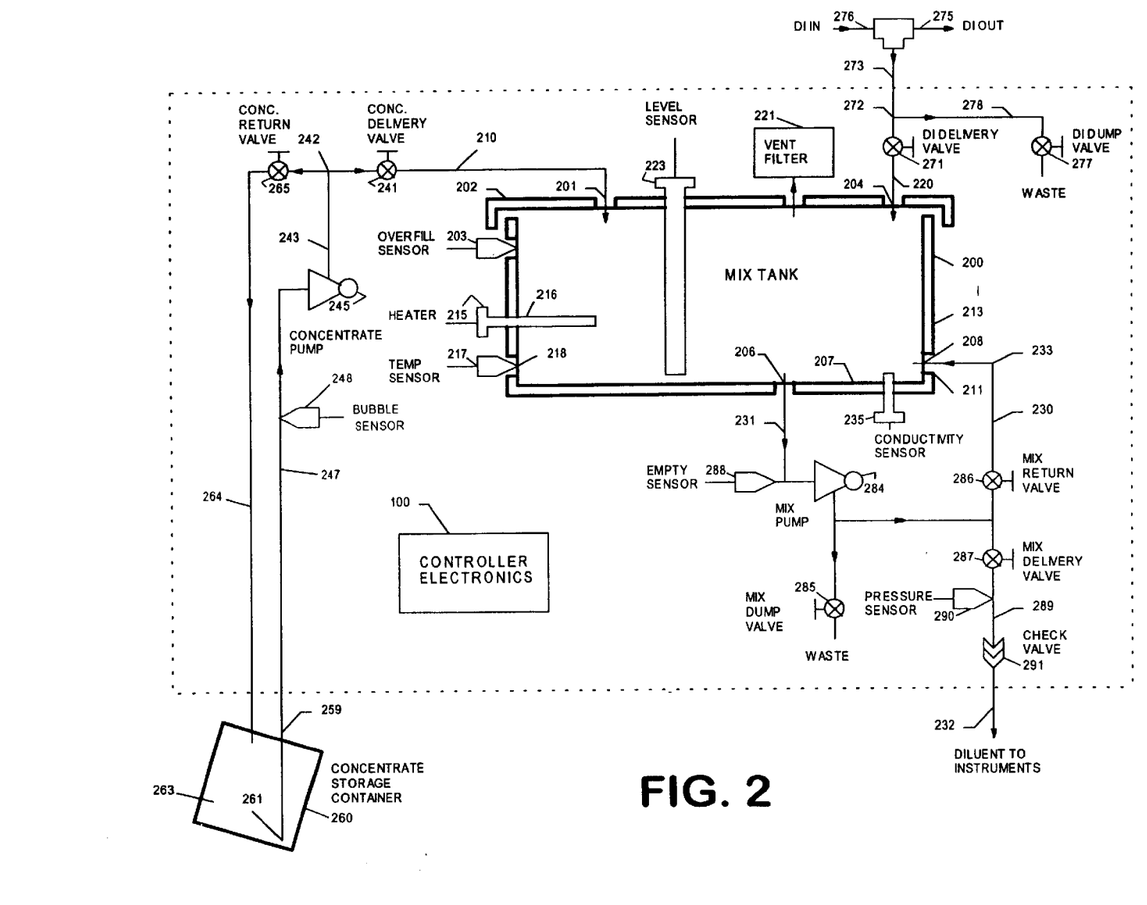
FIG. 2 shows the details of a solution mixing container, associated concentrate and diluent transport paths, and a recirculation and delivery mixed solution output path.
Figure 3:
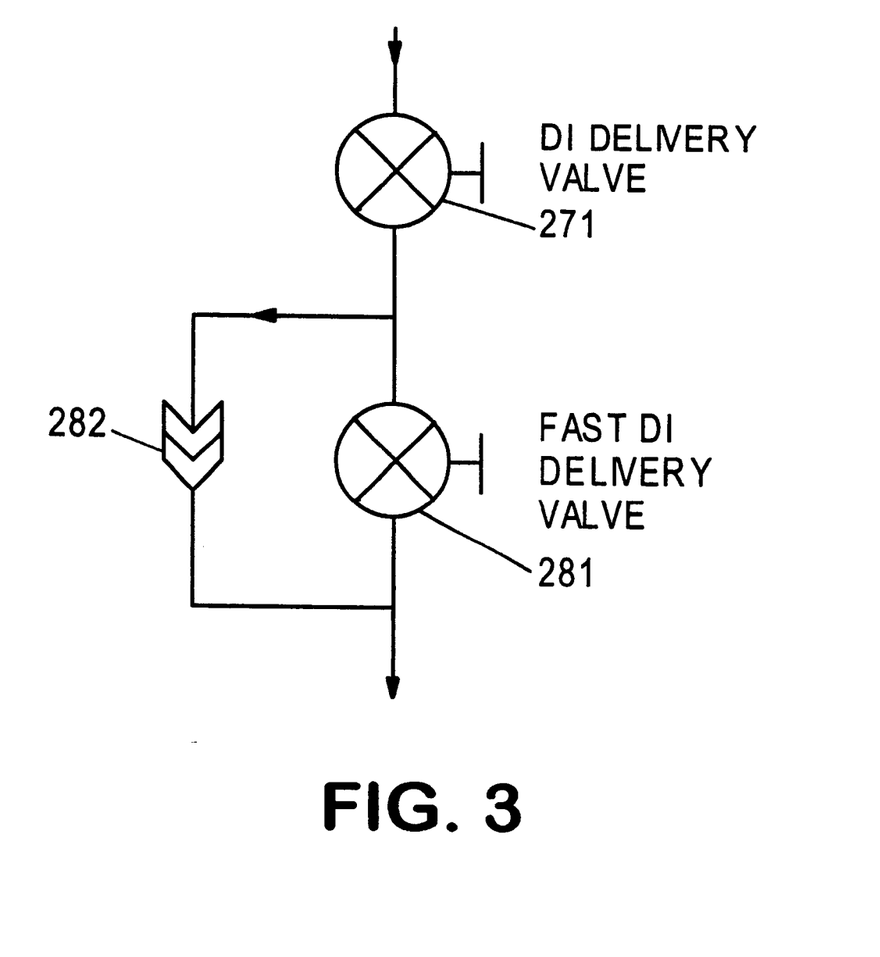
FIG. 3 diagrammatically illustrates a dual stage flow control device associated with a diluent supply valve to the solution mixing container of FIG. 2.

The overall architecture of the solution preparation and delivery apparatus of the present invention is diagrammatically illustrated in FIG. 1. A diluted solution mixing container or tank 10, to be described in detail below with reference to FIG. 2, is coupled to receive, mix and store each of a liquid concentrate of a prescribed component and a diluent. The liquid concentrate is stored in and extracted from a concentrate storage container 20, such as a plastic container or plastic lined container, under the control of a supervisory processor 100, for delivery over a controlled concentrate transport path 12 to the solution mixing container. As will be described in detail below with reference to FIG. 2, the controlled concentrate transport path 12 includes a set of valve and pump components, that enable it to controllably recirculate the (liquid concentrate) contents of the component storage container 20, in order to maintain the concentrate in a uniform or homogenous state prior to its being supplied to the solution mixing container 10.

The diluent is supplied to the mixing tank by way of a controlled diluent transport path 14, which is coupled to a source of pressurized diluent (deionized water), and is configured to controllably dispense the diluent into the mixing container 10. In addition, the diluent transport path 14 is configured to be controllably purged of potential contaminates prior to supplying the diluent to the mixing container 10, and thereby avoid the potential problem of having an unused diluent distribution line serve as a host for the growth of biological contaminants.

A mixed solution transport path 16 is coupled to the solution mixing container 10 and to a prepared solution delivery output port 18. The mixed solution transport path 16 is configured to actively recirculate and thereby homogenize the contents of the mixing container, during an iterative sequence of adding diluent to the mixing tank and conducting conductivity measurements, until the conductivity of the solution in the mixing tank reaches a target value required by a downstream instrument. The mixed solution transport path 16 is also configured to controllably actively pump out solution that has been prepared (mixed) and stored in the mixing container 10 to the output port 18. The output port 18 is coupled over an output line 22 to one or more solution on-demand storage reservoirs 24 associated with respective (analyzer) instruments 26.

An 'intermediate' waste container or transfer tank 30 may be coupled to the fluid transport paths 14 and 16 for storing purged waste liquid, to accommodate the case where the facility in which the mixing tank is installed has no readily accessible floor drain for the purpose. An on-demand valve-responsive mixed solution reservoir 24 for a respective instrument 26 is coupled to the mixed solution output port 18. An associated demand controller 28 is programmed to manage delivery of the mixed solution from the mixing container 10 to the on-demand reservoir 24 when its associated instrument (e.g., hematology analyzer) 26 requires additional (saline) solution.

Because the on-demand reservoir 24 is expected to remain connected to an associated instrument for a long period of time, it is placed in a protective tray 32. A set of leak detectors 36 is installed in the tray adjacent to a lower port of the reservoir 24, in order to monitor whether the outside of the reservoir is damp, contains a minor leak, or whether a massive leak has formed. A leak condition is determined by measuring whether the impedance between sensor pairs is less than a prescribed value. Since each sensor pair has a dedicated set of terminal leads, the demand controller can monitor each sensor pair separately to determine that the sensors are active.

Figure 7:
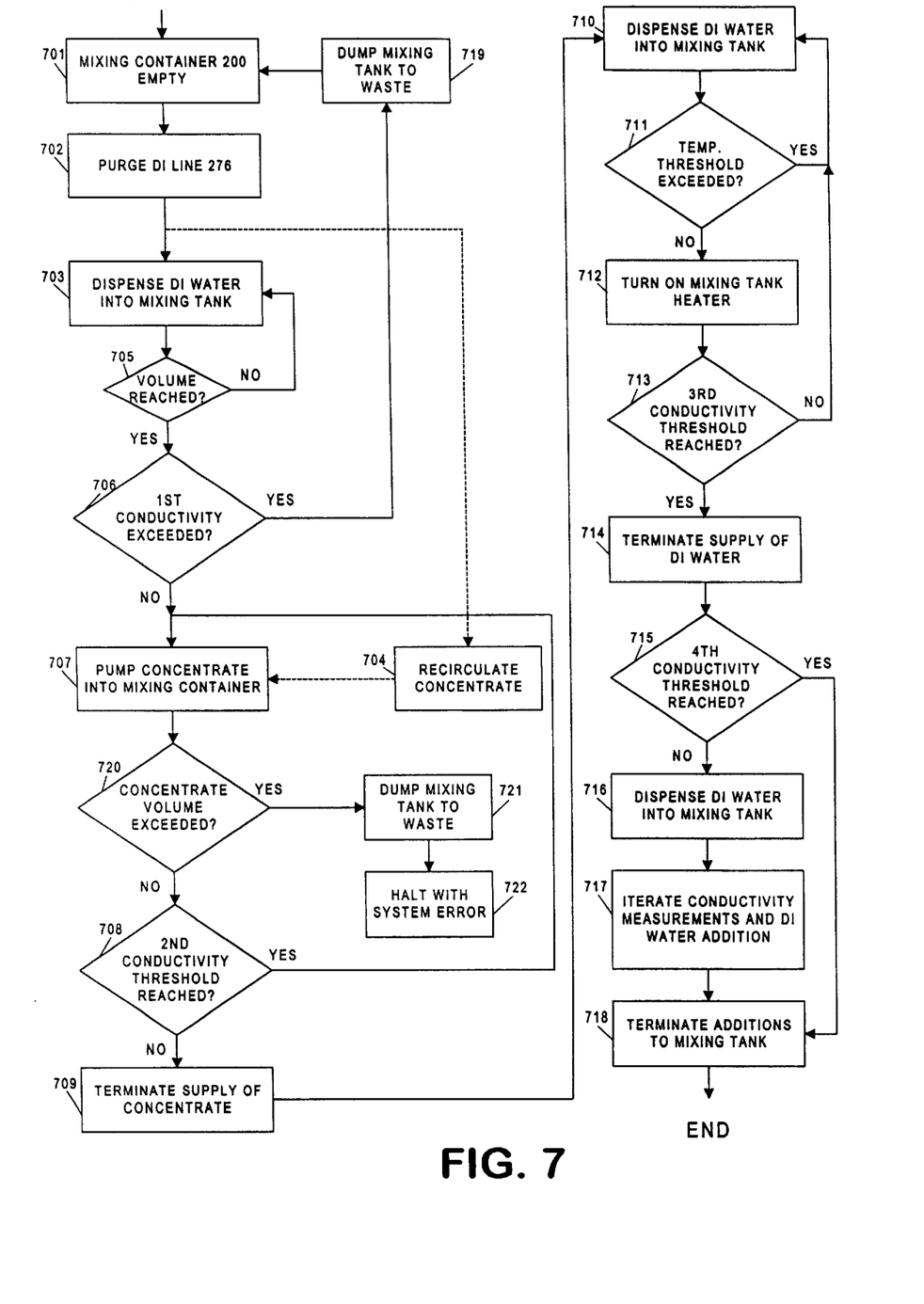
FIG. 7 is a flow chart associated with operation of the solution preparation and delivery apparatus of the invention.

As will be described in detail below with reference to the flow chart of FIG. 7, the preparation, mixing and delivery sequence executed by the solution preparation and supply apparatus of the invention employs a plurality of conductivity thresholds to reach a target solution conductivity associated with desired (saline) concentration. This readily allows the invention to comply with a solution specification (such as a constant conductivity ISOTON® diluent (Beckman Coulter, Inc., Fullerton, Calif.)) associated with an instrument, such as a hematology analyzer, that uses changes in conductivity of a fluid in a flow measurement aperture to count and recognize blood cells.

Referring now to FIGS. 2–6, the solution preparation and supply apparatus of FIG. 1 is diagrammatically shown in detail as comprising a solution mixing container or tank 200 having a first input port 201, to which a first fluid (concentrate) transport path 210 supplying a component or concentrate is coupled. The first input port 201 is installed at an upper or top portion 202 of the mixing tank 200 above the location of a full level (or overfill) sensor 203, to prevent siphoning of the contents of the mixing container back into the fluid transport path 210. When the level of the solution reaches that of the overfill sensor 203, the overfill sensor signals the system control processor 100 to terminate the delivery of either concentrate or diluent into the mixing container. A second input port 204 is coupled to a second fluid (diluent) transport path 220 that controllably supplies a diluent into which the concentrate is to be dispersed. Like the first input port 201, the second input port 204, is installed at the top or lid portion 202 of the mixing tank above the full level sensor 203, to prevent siphoning of the contents of the mixing container back into the diluent transport path 220.

The mixing container 200 further includes an output port 206 at a floor region 207, and being coupled to a solution extraction section 231 of a third fluid transport path 230 that controllably delivers the prepared solution to a solution delivery or output port 232. A return line from a recirculation section 233 of the third fluid transport path 230 is ported to a recirculation inlet port 208 at a lower region 211 of a sidewall 213 of the mixing container adjacent to the floor region 207. A concentration sensor 235 is coupled to a floor location of mixing container 200 between the recirculation inlet port 208 and the output port 206. In a non-limiting preferred embodiment, the concentration sensor 235 is implemented by means of a conductivity sensor having a four contact, in-line configuration. For performing a conductivity measurement, the outer two electrodes are driven with a square wave test signal, while their adjacent interior pair of electrodes are employed to measure conductivity of the solution.

Locating the sensor 235 between ports 206 and 208 ensures that, as solution is recirculated from the output port 206 through the third fluid transport path 230 and back into the mixing container by way of recirculation inlet port 208, it will be swept across or past the sensor contacts. This sweeping flow action of the recirculated solution across the sensor contacts serves to prevent the formation of bubbles on the interior sensor electrodes that might otherwise introduce noise into the sensor output signals. Such a noise-inducing bubble formation is a typical problem in two contact sensor configurations used in salt solutions of moderately high conductivity.

A solution heating element 215 is installed at a generally lower sidewall region 216 of the mixing container. Associated with the heating element 215 is a solution temperature sensor 217 installed at a lower sidewall region 218 of the mixing container adjacent to the floor region 207. Each of the heating element and the temperature sensor are coupled to the system processor 100. The heating element 215 is controlled so as to maintain the solution at a nominal temperature required by a downstream instrument for optimum performance. In this regard the temperature of the solution delivered from the mixing container should be nearly the same as solution held in reserve by the instrument.

The mixing container 200 is vented to the atmosphere through a vent filter 221 which is installed in the lid 202 to prevent airborne contaminates from being drawn into the mixing container, when the solution is being pumped out to a downstream instrument. A vertical level sensor 223 is coupled to the control processor 100 and provides an indication of the level and thereby volume of solution in the mixing tank 200.

The first (component or concentrate) fluid transport path 210 through which concentrate is supplied to the input port 201 includes a processor-controlled component delivery valve 241 installed downstream of a joint 242 of an output line 243 from a positive displacement pump 245, to an input of which a component supply line 247 is coupled. The use of a positive displacement pump avoids having to prime the pump. In a non-limiting, but preferred implementation, the pump 245 is of the type that employs a recirculating pinch roller, to avoid contamination between the pump and the concentrate in the line 247, as the pinch roller acts on the line tubing directly.

The component (concentrate) supply line 247 is coupled with a bubble sensor 248 and is terminated by a pick-up tube 259 which extends into a concentrate container 260. The bubble sensor 248 is used to detect when the container 260 is empty. If the bubble sensor detects that container 260 has become emptied of concentrate in the course of delivery of concentrate to the main container 200, the filling operation is suspended and an alarm indication is provided, to allow the user to replace the concentrate container 260. A concentrate recirculation sequence is initially performed to clear the bubble and homogenize the concentrate in the container 260 before resuming delivery of concentrate to the main container 200.

The concentrate supply container 260 may comprise an industry standard generally 'cube'-shaped container, such as a CUBITAINER® plastic container (Hedwin Corp., Baltimore, Md.), in which a solution of a prescribed concentration of a component, such as sodium chloride, is available from a commercial concentrate supplier. Preferably the concentrate container 260 is installed in a support assembly that allows the container to be oriented (e.g., tilted) so that the distal end 261 of the pick-up tube 259 may be located at a bottom corner of the container 260 for maximum concentrate extraction.

The transport path 210 further includes a return line 264, which extends from the joint 242 of the output line 243 and is ported to an upper portion of the concentrate container 260 for concentrate recirculation purposes. The return line 264 is terminated at an upper portion of the concentrate container 260 above its full mix level to prevent potential siphoning action back through the line 264. A processor-controlled return valve 265 is installed in the return line 264 downstream of the joint 242.

Opening the return valve 265, closing the delivery valve 241 and operating the pump 245 for a prescribed period of time prior to delivering the concentrate to the main container 200 serves to recirculate the concentrate in the container 260 and ensures that the concentrate will have a uniform consistency when drawn from the container 260 and delivered to the mixing container 200.

The second fluid (diluent) transport path 220 that controllably supplies diluent to port 204 of the mixing container, includes a processor-controlled diluent delivery valve 271 installed downstream of a joint 272 of a diluent supply line 273, which extends from a branching connector, such as a T-joint or fitting 275 installed in a main, pressurized diluent supply line 276 which transports a diluent, such as deionized (DI) water from a reverse osmosis source and conforming with a prescribed DI water specification. The T-fitting 275 allows multiple containers 200 to be cascaded or distributed in parallel along the diluent supply line 276. Where the main container 200 is the last or terminal container along the supply line, there is no T-fitting and the supply line 276 is coupled directly to the unit.

A DI purge valve 277 is installed in a section of line 278 extending from the joint 272, and is used to controllably dump diluent to a waste container (not shown in FIG. 2), so as to clear any diluent that may have accumulated or stagnated in the supply line, and thereby avoid the potential problem of having an unused DI distribution line act as a host for the growth of biological contaminants.

The diluent delivery valve 271 may be configured to facilitate filling different sized main containers. For a relatively large capacity main container, which does not require a fine or vernier control of the introduction of diluent, a single valve may be used. However, for a smaller capacity main container, where fast/slow control of introduction of diluent is necessary, the delivery valve 271 may be augmented by dual stage flow control device, as diagrammatically illustrated in FIG. 3. In this augmenting device, a fast fill valve 281 is coupled in parallel with a restrictor 282, to provide for either fast or slow delivery of diluent to main container 200.

The solution extraction section 231 of the third fluid transport path 230, which is ported to the mixing container's output port 206 is coupled to a (positive displacement impeller type) mixing/recirculation pump 284, the output of which is coupled to each of a mix dump or waste valve 285, a mix return valve 286 and a mixed solution delivery valve 287. A bubble sensor 288 is installed in the solution extraction section 231 upstream of the pump 284, and serves to detect when the mix tank is empty. In this event, the control processor either turns off or does not turn on the pump 284 for recirculation (mixing) or diluent delivery.

The mix dump valve 285 is located in the lowest point of the solution recirculation loop and is ported to a waste container (not shown). The waste valve 285 enables diluent that does meet specifications to be dumped. The valve is also opened for a prescribed period of time, if the sensor 288 detects that the mixing container 200 is empty and diluent is being drawn into the tank. This allows any unknown elements to be swept out or purged from the tank and the recirculation lines. Since the mixing pump 284 is an impeller type device, fluid will pass by without the pump operating into waste.

The mixed solution delivery valve 287 is ported to an output line 289, to which a pressure sensor 290 is coupled and containing a check valve 291. The pressure sensor 290 is used to sense whether a downstream utility device (e.g., blood analyzer) is drawing solution from the output port 232, while the check valve 291 allows the outputs of plural units to be connected together and realize a redundant system. If the pressure in the output line 289 drops below a preset value, the mixing pump 284 is turned on, and solution is pumped out of the mixing container 200 to the demanding device. The output line 289 is ported to the mixed solution delivery port 232.

Figure 4:
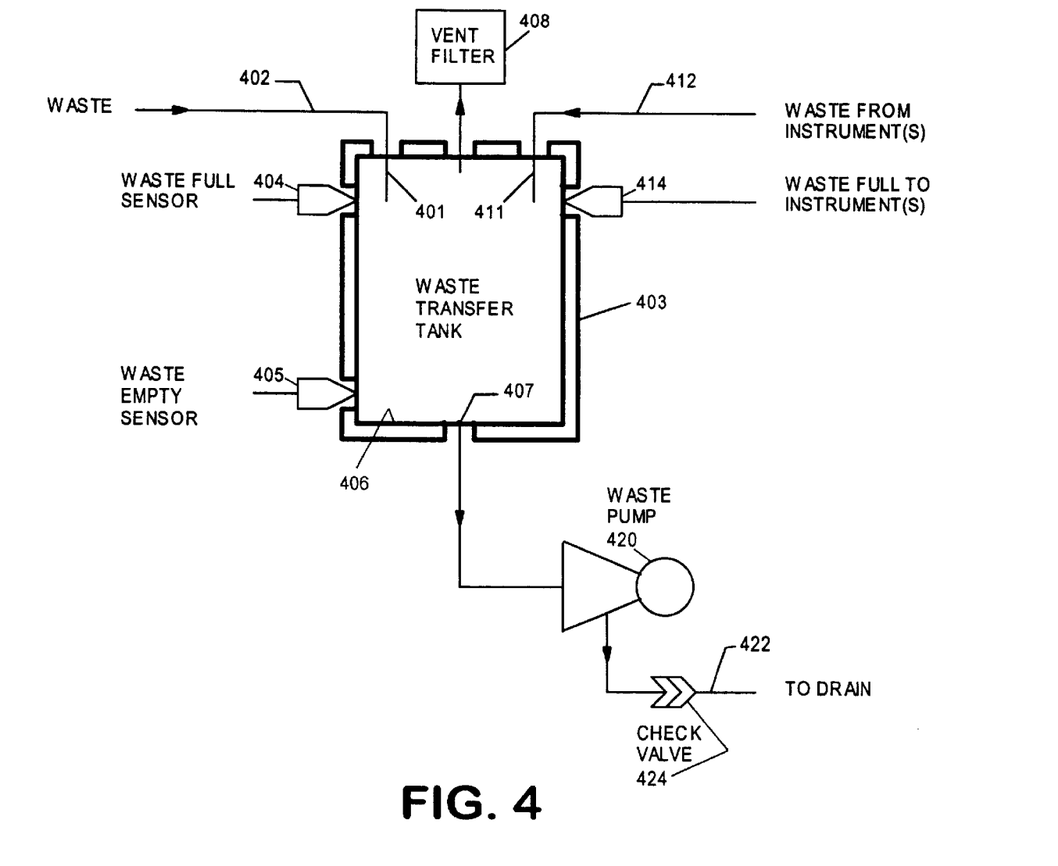
FIG. 4 diagrammatically illustrates an intermediate waste container.

FIG. 4 diagrammatically illustrates an optional 'intermediate' waste container/tank 400, to which the DI purge valve 277 and the mixing tank waste valve 285 may be ported, in the event that the solution delivery and mixing apparatus of the invention is to be installed in a facility having no (floor) drain to which the apparatus may be directly purged. As shown in FIG. 4, the waste tank 400 has a first input port 401 to which a gravity fed drain line 402 from either or both of DI waste valve 277 mixing tank purge valve 285 may be coupled. The waste tank 400 also has a second input port 411 to which a gravity fed drain line 412 from one or more instruments served by the solution preparation and mixing tank 200 may be coupled. The waste container 400 is vented to the atmosphere through a vent filter 408 installed in the lid 402 to prevent the release of airborne contaminates when the waste container is being filled with waste material.

The input ports 401 and 411 are installed at a top portion 403 of the waste tank above the location of a full level sensor 404, to prevent siphoning of the contents of the waste container back into the two waste input lines. When the level of the waste container 400 reaches that of the full sensor 404, that sensor signals the system control processor 100 to terminate delivery of waste from either the solution preparation and delivery apparatus, or from an instrument into waste tank 400. An empty sensor 405 is installed adjacent to a floor region 406 of the waste tank.

The full and empty sensors are used by the system control processor to control a positive displacement pump waste removal pump 420, coupled to an output port 407 in the waste container floor 406. An instrument waste full sensor 414 installed at the level of the full sensor 404 is opto-isolated to the prepared solution receiving instruments to ensure that should the waste in the container 400 not be emptied, the instruments will stop presenting additional waste product. The output of the waste removal pump 420 is coupled to a drain line 422 through a check valve 424, to prevent reverse flow back to the pump. The waste removal pump 420 has sufficient pumping capability to pump waste fluid out of the waste container 400 over a drain line having a prescribed head (e.g., a ten foot relative elevation), so allow its use with a waste discharge line that extends across a ceiling to a floor drain.

Figure 5:
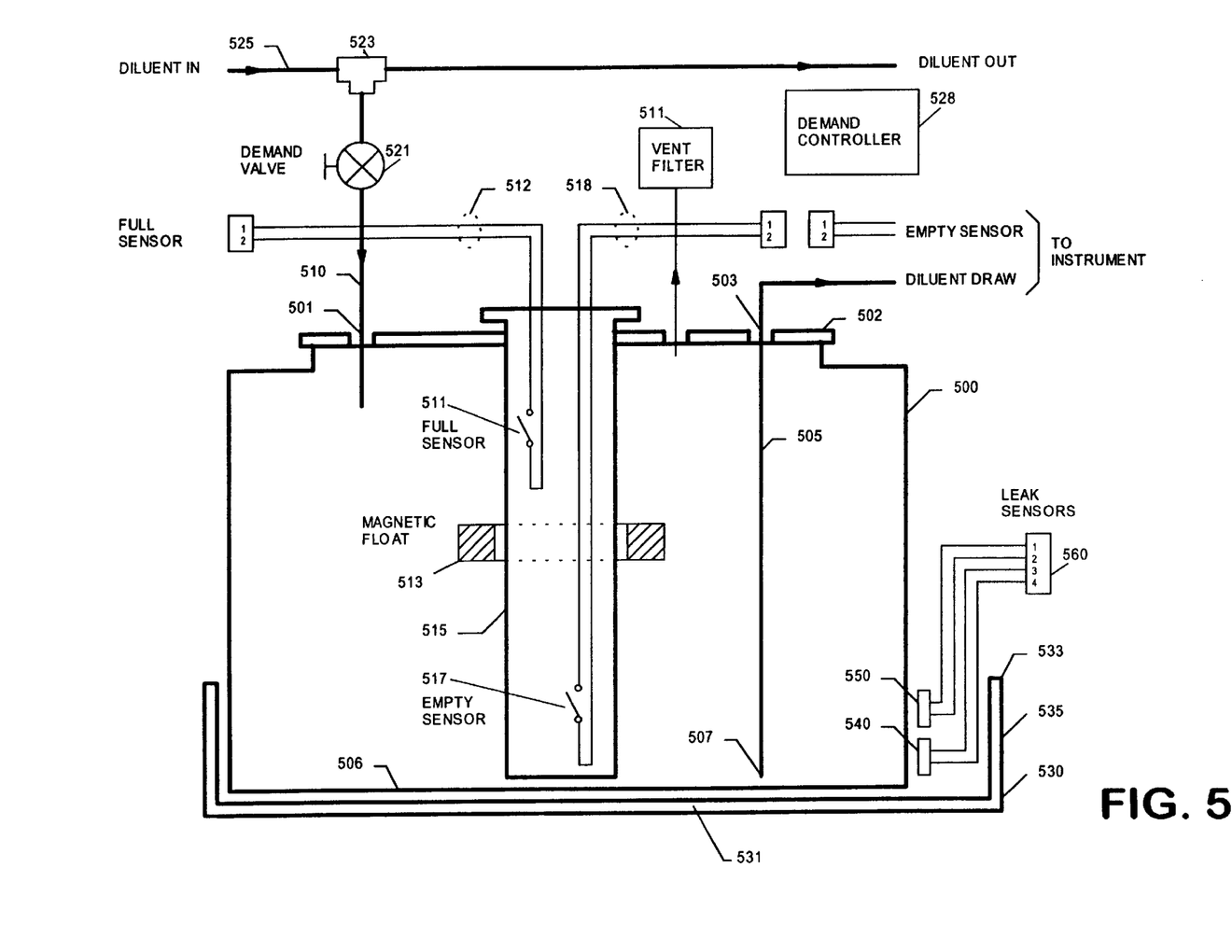
FIG. 5 diagrammatically shows the configuration of a demand valve-responsive mixed solution reservoir.

FIG. 5 diagrammatically illustrates a demand valve-responsive mixed solution reservoir 500 associated with a respective instrument, coupled to the solution delivery port 232 of the mixing container 200 of FIG. 2. Like the concentrate container 260, the instrument reservoir 500 may be configured as an industry standard CUBITAINER® plastic container, and includes an input port 501, to which mixed solution from the mixing container is controllably supplied. The input port 501 is installed (e.g., threaded into an opening) at a top or lid 502 of the reservoir 500 above a full level sensor 511, such as a magnetically activated reed switch, to prevent siphoning of the contents of the reservoir back into an input line 510. The reservoir lid 502 may be secured by way of a threaded collar ring (not shown) to prevent outside entry of potential contaminates.

When the level of the solution in the reservoir rises to that of the full sensor reed switch 511, installed at an upper portion of a generally hollow vertical column member 515, the full sensor signals an associated demand controller 528 through a signal line 512, so that the demand controller will close a demand valve 521 installed in the input line 510, and thereby terminate delivery of solution to the reservoir 500. The demand controller 528 contains processor-controlled circuitry that is programmed to manage delivery of the mixed solution from the mixing container 200 to the reservoir when its associated instrument (e.g., hematology analyzer) requires additional (saline) solution. Although a standard CUBITAINER® plastic container contains biological growth inhibitors, as a precautionary measure, the reservoir may be replaced at routine intervals, to ensure that any biological growth will not go unchecked.

The reservoir 500 further includes an output port 503, for example threaded into an opening in the lid 502, through which a solution draw line 505 is ported to the instrument. The solution draw line has a distal end 507 located at a bottom region of the reservoir 500 for maximum solution extraction. The solution reservoir is vented to the atmosphere through a vent filter 511 installed (e.g., threaded into a bore) in the lid 502, to prevent airborne contaminates from being drawn into the reservoir, when the solution is drawn out by a downstream instrument. A vertical level sensor 513, such as a magnetic float ring, surrounds the generally hollow vertical column member 515, which is inserted through the reservoir lid 502 to the bottom 506 of the reservoir. The magnetic float ring 513 rides on the surface of the solution stored in the reservoir. An empty sensor 517, which, like the full sensor 511, may comprise a magnetically operated reed switch, is installed in a lower end of the vertical column member 515. When the level of the solution in the reservoir drops below that of the empty sensor 517, the empty sensor signals the demand controller 528 through a signal line 518, so that the controller will open the demand valve 521 to supply solution into the reservoir.

To maintain a greater reserve supply in the reservoir, 500, the demand controller, 528, can activate the demand valve at regular intervals of time if the full sensor, 511, indicates less than full. Since the attached instrument draws the blood sample carrier fluid at a known maximum rate, then more frequent fill cycles can occur which keeps a longer operational reserve to the instrument should the delivery system fail. Preferably, the storage reservoir is refilled through a demand valve selectively activated by the passage of time or empty condition so as to keep the reservoir maintained at greater than about 40% filled and preferably greater than about 60% filled.

The solution input line 510 through the demand valve 521 is installed downstream of a T-joint or fitting 523 installed in a main solution supply line 525 which is coupled to the solution delivery port 232 and transports the mixed solution to one or more instruments. As in the supply of DI diluent to the mixing tank 200, described above, the T-fitting 523 in the solution supply line from the mixing tank allows multiple instruments to be cascaded or distributed in parallel along the mixed solution supply line 525. Where the reservoir 500 of interest is the last or terminal reservoir along the line 525, there is no T-fitting and the supply line 525 is coupled directly to the reservoir.

Because the mixing solution reservoir is expected to remain connected to an associated instrument for a long period of time, it is placed upon the floor or bottom 531 of a protective tray 530. The tray contains a set of leak detectors 540 and 550 located adjacent to a lower port of the reservoir, in order to prevent the occurrence of an excessive leak associated with replenishment of the solution in the reservoir. The tray 530 is preferably formed of leak proof material, with the leak sensors 540 and 550 positioned just below the top 533 of a sidewall 535 of the tray.

Figure 6:
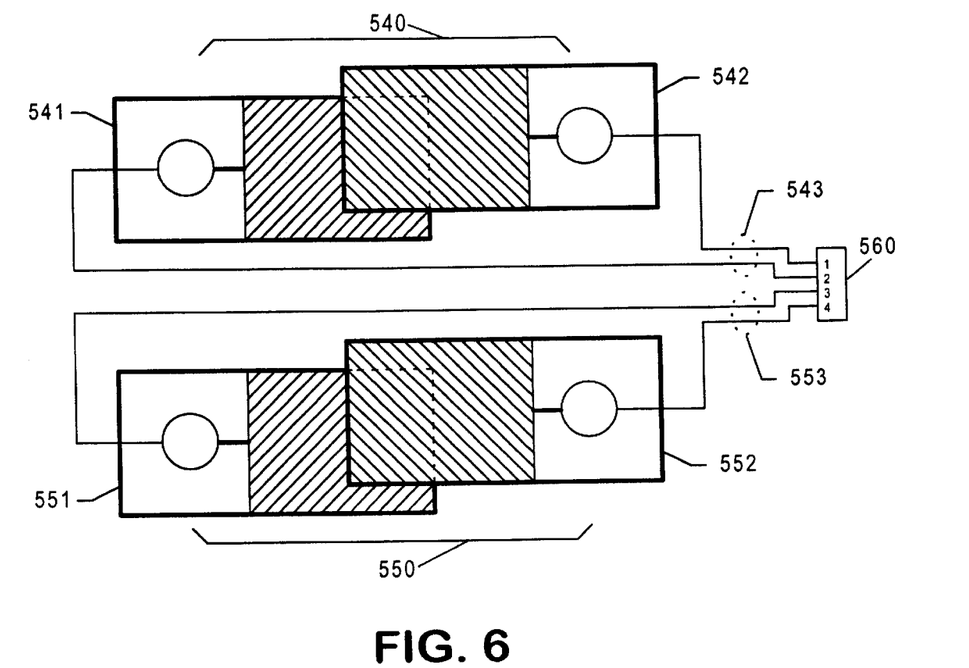
FIG. 6 shows the configuration of a set of leak sensors for the reservoir of FIG. 5.

The leak sensors 540 and 550 may be configured as shown in FIG. 6, being formed of respective pairs of disposable EKG (electrocardiogram) electrodes 541, 542 and 551, 552, coupled by way of terminal lead pairs 543 and 553 to a suitable connector 560. EKG electrodes customarily have a snap electrical connection fitting and a conductive adhesive Ag/AgCl printed surface. The electrodes of each pair partially overlap and are bonded to each other, and may be adhesively bonded to the tray sidewall 535. In this configuration, each pair of electrodes is able to monitor both whether outside of the reservoir is damp, contains a minor leak, or whether a massive leak has formed. A leak condition is detected by measuring whether the impedance between the sensor pairs is less than a prescribed value. Since each sensor pair has a dedicated set of terminal leads, the demand controller can monitor each sensor separately to determine their presence.

The operation of the present invention will now be described with reference to the routine presented in the flow chart of FIG. 7. As described briefly above, the operational sequence executed by the solution preparation and supply module apparatus of the invention operates on the basis of solution conductivity. This allows the invention to comply with a solution specification (such as a constant conductivity isotonic solution) associated with an instrument, such as a hematology analyzer, that uses changes in conductivity of a fluid in a flow measurement aperture to count and recognize blood cells. To this end, the operational control sequence of the present invention employs a number of conductivity thresholds to reach the target conductivity for a deliverable solution.

The processing routine starts at step 701 with the mixing container 200 being empty in preparation for a new fill and mix sequence prior to delivery of mixed (isotonic) solution to one or more downstream instrument reservoirs. At step 702, the control processor operates the DI purge valve 277 in order to drain DI water in the line 276 for sufficient period of time to ensure that any potential biological contaminants in the diluent (DI water) line 276 are removed as waste (either directly to an associated drain or the 'intermediate' waste tank 400). As pointed out above, although the T-fitting 275 allows multiple solution mixing containers 200 to be cascaded or distributed in parallel along the diluent supply line 276, a respective unit assumes that it is at the end of a 'dead' line and therefore must clean its line before each use.

Once it has completed purging the DI line by closing the DI purge valve, it opens the diluent delivery valve 271, as shown at step 703, so that (DI) diluent will be dispensed into the mixing tank 200 through diluent input port 204. Where the diluent delivery valve 271 is configured as a dual stage flow control device, illustrated in FIG. 3, this initial introduction of a substantial volume of diluent to the mixing container 200 may be conducted by way of the fast fill valve 281. Subsequent infusion of DI water, during iterative DI dispense and conductivity measurement steps, to be described, may be by way of the restrictor 282, to provide for a vernier/slow delivery of diluent to the mixing tank 200.

As diluent is being added to the mixing tank, the component (concentrate) delivery valve 241 in the concentrate fluid transport path 210 to the mixing container is maintained closed, the return valve 265 is held open, and the concentrate pump 245 in the output line 247 from the concentrate container 260 is turned on in step 704. This serves to recirculate and thereby ensure a homogeneous condition of the concentrate in the concentrate container 260, prior to its being supplied to the mixing container 200.

In query step 705, the output of the level sensor 223 is monitored to determine whether the volume of the contents (here only diluent) of the mixing container 200 has reached a prescribed value (e.g., three gallons). Once the answer to query step 705 is YES, with each of waste valve 285 and mixed solution delivery valve 287 in the third fluid transport path 230 closed, and with the mix return valve 286 open, the recirculation and deliver pump 284 is turned on to recirculate the contents of the mixing tank 200 and thereby cause a fluid flow past the electrodes of the concentration sensor 235, the output of which is monitored by the control processor.

In query step 706, the conductivity of the contents of the mixing tank 200 is examined. If it is above a first threshold, namely, too high (the answer to query step 706 is YES), it is inferred that the diluent has somehow become contaminated, so that the waste valve 285 is opened to dump the diluent to waste, step 719, and the routine loops back to step 701. The reasoning for this action is that if the mixing tank is contaminated, the liquid typically become more conductive. For example, deionized water should have a minimum of conductivity of less than 0.1 micro Siemens. However, if the conductivity of the contents of the mixing tank 200 is less than the first threshold and therefore acceptable (the answer to query step 706 is NO), then the routine transitions to step 707.

In step 707, the operational states of the concentrate delivery valve 241 and the return valve 265 in the concentrate fluid transport path 210 are reversed, so that the concentrate pump 245 will now pump concentrate into the mixing container 200. The recirculation and deliver pump 284 remains turned on, so as to recirculate the contents of the mixing tank 200 (which now includes concentrate being added to the previously supplied DI diluent).

This method of diluting the concentrate insures that the temperature dependent conductivity hysteresis cycle of a salt solution begins at a known condition. The initial conductivity is very low, such as identified with deionized water. This is followed by a high conductivity, typically greater than 30 milli Siemens, when the concentrate is delivered to the mixing tank. With the addition of the deionized water, the conductivity of the mixture approaches the final target value.

During the supply of concentrate to the mixing tank in step 707, the conductivity of the contents of the mixing tank 200 is examined and the volume of the mixing tank is measured, in query step 708. Until the volume of the mixing tank (as monitored by level sensor 223) indicates to the control processor that a volume of concentrate exceeding a prescribed amount, query step 720, has been dispensed into the mixing tank, or as long as the conductivity of the contents of the mixing tank is less than a second threshold (the answer to query step 708 is NO), concentrate continues to be delivered over the concentrate fluid transport path 210 into the mixing container 200, and the recirculation and deliver pump 284 continues to recirculate the contents of the mixing tank 200.

However, when the answer to query step 708 is YES, the routine transitions to step 709, wherein the operational states of the concentrate delivery valve 241 and the return valve 265 in the concentrate fluid transport path 210 are again reversed, and the pump 245 is turned off, so that the supply of concentrate to the mixing tank is terminated. If the concentrate volume has been exceeded, query step 720, then the mixing tank is emptied, step 721, and a system failure condition is posted, step 722. In such case, the system will not continue until reset or service is provided.

Next, in step 710, the diluent delivery valve 271 is reopened, so that additional DI diluent is dispensed into the mixing tank 200. At the same time, the recirculation and delivery pump 284 remains turned on, so as to recirculate the contents of the mixing tank 200, as the additional DI water is to the mixture. At query step 711, the temperature of the contents of the mixing tank, as monitored by temperature sensor 217, is examined. If the temperature of the mixture is less than a prescribed nominal value (e.g., on the order of 25° C.), the mixing tank heating element 215 is turned on in step 712, so as to bring the temperature of the solution up to nominal. While this heating step has no impact on the mixing operation, it is desirable from a standpoint of delivering solution to the instrument reservoir 500 without causing a thermal change in the contents of the reservoir.

In addition to monitoring the temperature of the contents of the mixing tank, the conductivity of the contents of the mixing tank 200 is compared with a third conductivity threshold in query step 713, as additional DI water is dispensed in step 710. Once the answer to query step 713 is YES, indicating the solution conductivity is within a prescribed window (e.g., 95%) of a target conductivity value, the DI inlet valve 271 is closed, so as to terminate the supply of diluent to the mixing tank. In step 714, the contents of the mixing tank is recirculated through the third fluid transport path 230, to ensure homogeneity of the solution.

Next, in query step 715, the conductivity of the solution is compared with a fourth threshold, for example, one closer to (on the order of 99% of) target conductivity. If the answer to query step 715 is NO, indicating that the conductivity of the solution has not yet reached the fourth threshold (which is expected to be the case), then in step 716, the DI inlet valve 271 is reopened, so as to dispense additional diluent to the mixing tank. If the answer to query step 715 is YES (highly unlikely, although possible), the routine proceeds to step 718. In the course of step 716, the contents of the mixing tank continues to be recirculated through the third fluid transport path 230, to ensure homogeneity of the solution. It should be noted that after each iterative infusion of DI water, the conductivity of the solution will drop somewhat, as the recirculation of the solution makes the mixture more homogeneous.

This iterative addition of DI water and conductivity measurement process continues in step 717, until the conductivity measurement indicates that the conductivity of the homogeneous solution in the mixing tank is exactly at the target value. Once the conductivity of the homogeneous solution in the mixing tank is at the target value, as shown by step 718, there is no further infusion of diluent and the solution is ready for delivery to one or more of the instrument reservoir 500 of FIG. 5. Solution is delivered to the solution delivery port 232 and thereby to the (isotonic) solution supply line 525 by the mixing/recirculation pump 284, with the mix return valve 286 closed and mixed solution delivery valve 287 opened.

As described above, the demand controller 528 of each mixed solution reservoir 500 manages delivery thereto of the mixed solution supplied over the solution delivery line 525 from the mixing container 200, in accordance with the (on-demand) solution requirements of its associated instrument (e.g., hematology analyzer). When the level of solution in the reservoir drops below that of the empty sensor 517, or the full sensor, 511, states not full, the demand controller opens the demand valve 521 to draw additional solution from the supply line 525 into the reservoir. Once the level of the solution in the reservoir rises to that of the full sensor 511, the demand controller closes the demand valve 521 to terminate delivery of solution to the reservoir 500. As note above, the use of branching connectors, such as T-fittings, in the solution supply line from the mixing tank allows multiple solution utility instruments to be distributed in parallel along the mixed solution supply line 525. The demand controller operates independently of the attached hematology instrument so that the attached instrument perceives no changes to its operation and regulatory configuration approvals.

Figure 8:
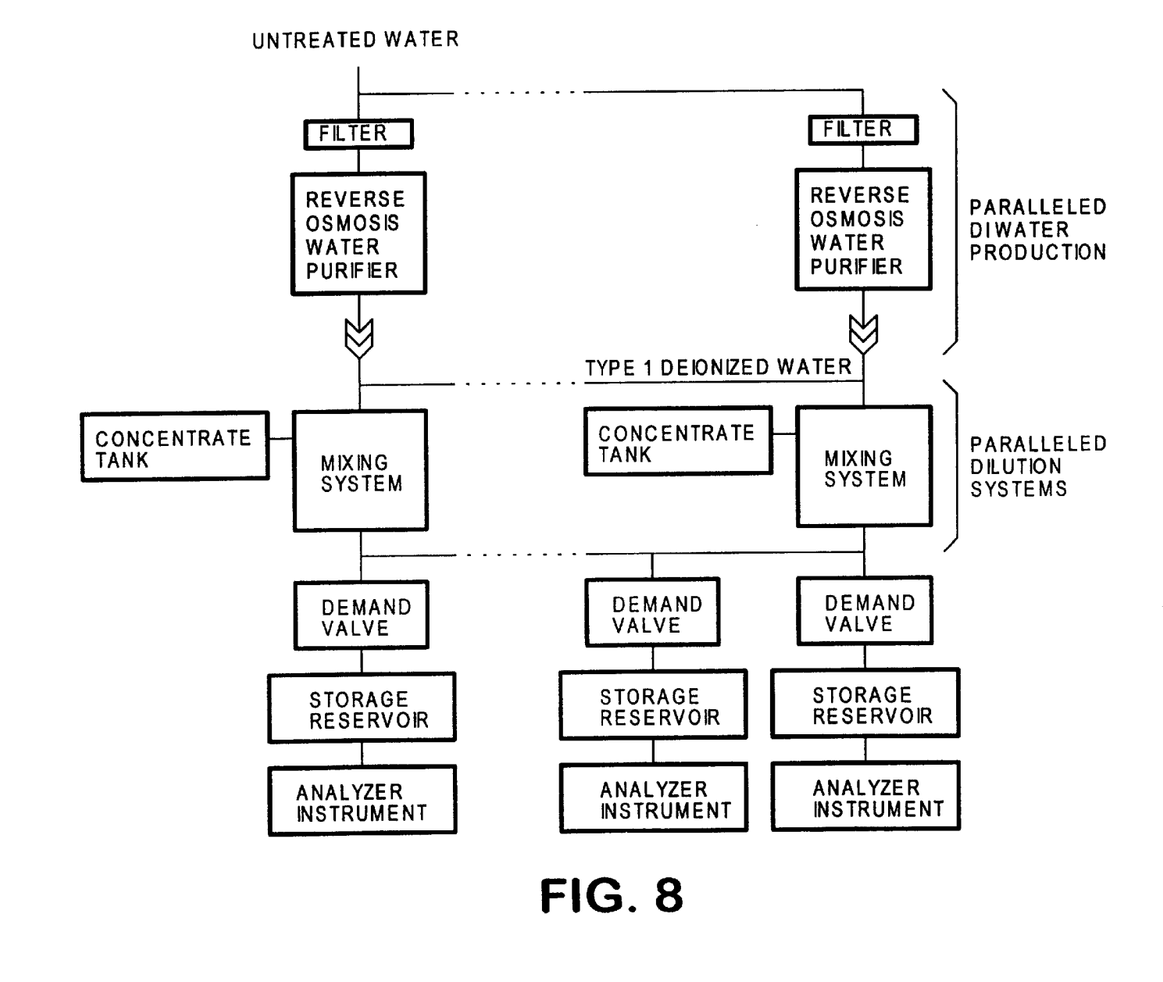
FIG. 8 is a diagram of multiple apparatus operatively linked together operatively linked together to provide continuous process operation in the event that any one of the apparatus fails to perform.

As will be appreciated from the foregoing description, the demand for a relatively compact solution preparation apparatus, that is not only capable of high throughput and reduced operating time, but may be readily interfaced with one or more instruments, such as hematology analyzers, is readily accommodated by the concentrate diluting and mixed solution delivery architecture of the invention. Because the operation of the apparatus is based upon measured conductivity of the solution in the mixing container, there is no need to conduct precursor volumetric measurements of either diluent or concentrate. Moreover, multiple apparatuses can be operatively linked together to provide continuous process operation in the event that any one of the apparatus fails to perform. A proposed configuration is shown in FIG. 8.

Advantageously, the concentrate transport path is configured to both homogenize and deliver concentrate to the mixing tank, while the diluent transport path is configured to be controllably purged of potential contaminates prior to supplying the diluent to the mixing container. Similarly, the mixed solution transport path is configured to recirculate and thereby homogenize the contents of the mixing container, and to actively pump out solution that has been mixed to a prescribed conductivity-based concentration, to one or more solution on demand storage reservoirs for respective instruments.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein, but intend to cover all such changes and modifications as are obvious to one of ordinary skill in the art.

What is claimed:

1. An apparatus for providing a solution of a diluent and a prescribed concentration of a component diluted therein comprising:
   a solution mixing container to which said component and said diluent are supplied, and from which said solution is controllably deliverable to a solution delivery port;
   a component storage container, in which said component is stored;
   a first fluid transport path, through which said component stored in said component storage container is controllably supplied from said component storage container to said solution mixing container;
   a component recirculation path through which said component stored in said component storage container is controllably recirculated from and back into said component storage container so as to maintain uniformity of said component in said component storage container;
   a second fluid transport path through which said diluent is controllably supplied from a source of said diluent to said solution mixing container;
   a second fluid transport path purger, which controllably purges said second fluid transport path of potential contaminates prior to said second fluid transport path controllably supplying said diluent to said solution mixing container;
   a third fluid transport path coupled to said solution mixing container and to said solution delivery port, and including a mixed solution recirculation path through which contents of said solution mixing container are controllably recirculated from and back into said solution mixing container, and a mixed solution extraction path through which contents of said solution mixing container are controllably delivered to said solution delivery port; and
   a controller which controls the operations of said first fluid transport path, said second fluid transport path, said second fluid transport path purger, said mixed solution recirculation path and said mixed solution extraction path in accordance with the conductivity of the contents of said solution mixing container, to realize therein said solution of said diluent and said prescribed concentration of diluted component.

2. The apparatus according to claim 1, wherein said second fluid transport path includes a variable rate of delivery path structure, that is controlled by controller to supply said diluent to said solution mixing container at a variable rate of delivery.

3. The apparatus according to claim 1, further comprising:
   a mixed solution storage reservoir having an input port to which contents of said solution mixing container are controllably delivered by way of said mixed solution extraction path, and an output through which solution stored in said reservoir is supplied to a solution utility device; and
   a leak sensor coupled with said mixed solution reservoir and being operative to generate an indication representative of a leakage condition of said reservoir.

4. The apparatus according to claim 3, further comprising:
   a waste container coupled to receive and store waste liquid from said second fluid transport path purger and waste contents of said solution mixing container from said third fluid transport path; and
   a fourth fluid transport path through which contents of said waste container are controllably removed from said waste container to a waste output port.

5. The apparatus according to claim 1, wherein said component storage container has a variable orientation relative to said first fluid transport path that enables substantially the entire contents of said component storage container to be extracted by said first transport path and delivered to said mixing container.

6. The apparatus according to claim 1, wherein said solution mixing container has a mixed solution output port coupled to a said mixed solution extraction path, and a mixed solution recirculation input port coupled to a said mixed solution recirculation path, and further including a mixed solution concentration sensor coupled to a location of said solution mixing container between said mixed solution recirculation input port and said mixed solution output port, so that as mixed solution is recirculated from said mixed solution output port through said mixed solution recirculation path and reenters said solution mixing container by way of said mixed solution recirculation input port, it flows through said solution mixing container past said mixed solution concentration sensor and prevents formation of an unwanted characteristic on said mixed solution concentration sensor.

7. The apparatus according to claim 1, wherein said second fluid transport path includes a diluent supply valve that is controlled by said controller to supply said diluent through said second fluid transport path to to said solution mixing container, and wherein said first fluid transport path includes a first fluid transport path valve arrangement that is controlled by said controller to supply homogenized component from said component storage container to said solution mixing container, and wherein said component recirculation path includes a component recirculation valve arrangement that is controlled by said controller to thereafter recirculate contents of said component storage container as said diluent is iteratively supplied to said solution mixing container by said second fluid transport path until the conductivity of contents of said solution mixing container satisfies a prescribed criterion.

8. The apparatus according to claim 1, wherein said second fluid transport path includes a diluent supply valve that is controlled by said controller to iteratively supply said diluent through said second fluid transport path to said solution mixing container, as contents thereof are recirculated by way of said component recirculation path, in accordance with a prescribed solution conductivity characteristic.

9. The apparatus according to claim 8, wherein said solution mixing container has a conductivity sensor coupled to a recirculation flow path therethrough, so that solution recirculated through said solution mixing container flows past said conductivity sensor and prevents formation of an unwanted characteristic thereon.

10. The apparatus according to claim 9, wherein said conductivity sensor has a four contact, in-line configuration.

11. The apparatus according to claim 9, wherein said mixed fluid extraction path of said third fluid transport path is coupled from said solution mixing container to said mixed solution delivery port through a check valve that allows multiple ones of said apparatus to be connected together and realize a redundant system for supplying said solution to one or more mixed solution storage reservoirs, from which said solution is supplied to respective utility devices.

12. A method for preparing a solution containing a diluent having a prescribed concentration of a component diluted therein comprising the steps of:

(a) providing a solution mixing container;

(b) providing a component storage container having a fluid concentration of said component;

(c) supplying said diluent to said solution mixing container over a diluent transport path, while recirculating contents of said component storage container through a component transport path to maintain mixture uniformity of said component stored in said component storage container;

(d) recirculating contents of said solution mixing container through a solution transport path, while controllably supplying fluid component stored in said component storage container through said component transport path to said solution mixing container; and (e) iteratively controlling the operation of said diluent and solution transport paths in accordance with the conductivity of the contents of said solution mixing container, to realize therein said solution of said diluent and said prescribed concentration of said component.

13. A method according to claim 12, wherein step (e) comprises iteratively causing said diluent fluid transport path to supply said diluent to said solution mixing container, while recirculating contents thereof by way of said solution transport path, in accordance with a prescribed solution conductivity characteristic.

14. A method according to claim 12, wherein step (e) includes monitoring the conductivity of contents of said solution mixing container by means of a conductivity sensor coupled to a recirculation flow path therethrough, so that solution recirculated through said solution mixing container flows past said conductivity sensor and prevents formation of an unwanted characteristic thereon.

15. A method according to claim 14, wherein said conductivity sensor has a four contact, in-line configuration.

16. A method according to claim 14, wherein said solution transport path is coupled from said solution mixing container to an output port through a check valve that allows solution transport paths of multiple solution mixing containers to be connected together and provide for redundant supply of said solution to one or more mixed solution storage reservoirs, from which said solution may be controllably supplied to respective utility devices.

17. A method according to claim 12, wherein step (e) comprises controllably varying the rate of supply of said diluent to said solution mixing container.

18. A method according to claim 12, further comprising the steps of:

(f) controllably delivering contents of said solution mixing container by way of said solution transport path to a storage reservoir having an output through which solution stored in said reservoir is supplied to a solution utility device; and (g) monitoring said storage reservoir for a potential leak condition.

19. A method according to claim 18, which further comprises (h) refilling a storage reservoir which is refilled through a demand valve selectively activated by the passage of time or empty condition so as to keep the reservoir maintained at greater than about 40% filled.

20. A method according to claim 12, further comprising the step of:

(f) selectively coupling at least one of said diluent and solution transport paths to a waste container.

21. A method according to claim 12, wherein step (b) comprises varying the orientation of said component storage container so as to enable substantially the entire contents of said component storage container to be extracted and delivered by said fluid component transport path to said solution mixing container.

* * * * *